United States Patent
Sato

(10) Patent No.: US 9,073,223 B2
(45) Date of Patent: Jul. 7, 2015

(54) ROBOT

(75) Inventor: Tomoyoshi Sato, Ibaraki (JP)

(73) Assignee: ATONARP INC., Hachioji-Shi, Tokyo (JP)

( * ) Notice: Subject to any disclaimer, the term of this patent is extended or adjusted under 35 U.S.C. 154(b) by 251 days.

(21) Appl. No.: 13/516,465

(22) PCT Filed: Dec. 22, 2010

(86) PCT No.: PCT/JP2010/007454
§ 371 (c)(1),
(2), (4) Date: Aug. 27, 2012

(87) PCT Pub. No.: WO2011/077730
PCT Pub. Date: Jun. 30, 2011

(65) Prior Publication Data
US 2012/0316677 A1   Dec. 13, 2012

(30) Foreign Application Priority Data
Dec. 22, 2009   (JP) .................. 2009-291000

(51) Int. Cl.
| G05B 19/418 | (2006.01) |
| B25J 13/08 | (2006.01) |
| G01N 27/62 | (2006.01) |
| G05D 1/02 | (2006.01) |

(52) U.S. Cl.
CPC ............ B25J 13/087 (2013.01); G01N 27/622 (2013.01); G05D 1/021 (2013.01); G01N 27/626 (2013.01); G05D 2201/0214 (2013.01)

(58) Field of Classification Search
CPC ................ G01N 27/622; B25J 13/087; G05D 2201/0214; G05D 1/021
See application file for complete search history.

(56) References Cited

U.S. PATENT DOCUMENTS

| 5,440,916 | A | * | 8/1995 | Stone et al. .................. 73/23.31 |
| 5,443,354 | A | * | 8/1995 | Stone et al. .................. 414/729 |
| 5,541,851 | A | * | 7/1996 | Sato et al. .................... 700/266 |
| 6,834,530 | B2 | * | 12/2004 | Kita et al. .................... 73/23.34 |
| 7,100,424 | B2 | * | 9/2006 | Wilson ......................... 73/31.05 |
| 7,420,664 | B2 | * | 9/2008 | Treado et al. ................. 356/72 |
| 7,526,970 | B2 | * | 5/2009 | Mawer ........................... 73/866 |

(Continued)

FOREIGN PATENT DOCUMENTS

| CN | 101241019 A | 8/2008 |
| CN | 101413811 A | 4/2009 |

(Continued)

OTHER PUBLICATIONS

English Translation of International Preliminary Report for Application No. PCT/JP2010/007454 dated Aug. 16, 2012.

(Continued)

*Primary Examiner* — Bhavesh V Amin
(74) *Attorney, Agent, or Firm* — Buchanan Ingersoll & Rooney PC

(57) ABSTRACT

A movable olfactory robot dog (1) includes an IMS unit (100) acquiring chemical substance-related information relating to chemical substances included in external air (19) respectively obtained from left and right nostrils (12L) and (12R), and an event monitoring unit (30) that determines the occurrence of an event and occurrence direction of the event relative to the robot dog (1) based on a change in the chemical substance-related information respectively acquired at the left and right nostrils (12L) and (12R).

19 Claims, 4 Drawing Sheets

(56) References Cited

U.S. PATENT DOCUMENTS

| | | | |
|---|---|---|---|
| 8,322,470 B2* | 12/2012 | Ohm et al. ................... | 180/9.32 |
| 2008/0165344 A1* | 7/2008 | Treado et al. .................. | 356/72 |
| 2013/0231779 A1* | 9/2013 | Purkayastha et al. ......... | 700/259 |

FOREIGN PATENT DOCUMENTS

| | | | |
|---|---|---|---|
| JP | 7-012671 A | 1/1995 | |
| JP | 7-260618 A | 10/1995 | |
| JP | 8-261893 A | 10/1996 | |
| JP | 9-127069 A | 5/1997 | |
| JP | 9-304319 A | 11/1997 | |
| JP | 2000-171424 A | 6/2000 | |
| JP | 2001-091416 A | 4/2001 | |
| JP | 2003-315298 A | 11/2003 | |
| JP | 2004-081851 A | 3/2004 | |
| JP | 2004-164303 A | 6/2004 | |
| JP | 2005-024426 A | 1/2005 | |
| JP | 2005-061836 A | 3/2005 | |
| JP | 2006-255402 A | 9/2006 | |
| JP | 2007-506083 A | 3/2007 | |
| JP | 2007-242056 A | 9/2007 | |
| WO | 2008/039996 A2 | 4/2008 | |

OTHER PUBLICATIONS

Asada et al., Development of an odor tracking robot with an array-type semiconductor gas sensor, The Japanese Journal of Taste and Smell Research, 13: 529-32 (2006).

Asada et al., Odor source localization using MOS-type gas sensor array, Papers of Tech. Meeting on Chem. Sens. Eng., CHS-07: 103-106 (2007). (English language abstract).

Fuma et al., Odor source localization robot using semiconductor type gas sensors, The Japanese Journal of Taste and Smell Research, 15: 617-20 (2008).

International Preliminary Report on Patentability from corresponding International Application No. PCT/JP2010/007454 dated Apr. 26, 2012.

International Search Report and Written Opinion from corresponding International Application No. PCT/JP2010/007454 dated Mar. 29, 2011.

Ishida et al., Odor-source localization robot mimicking animal behavior, Bio Engineering Koenkai Koen Ronbunshu, 10: 332-35 (1998).

Ishida et al., Odor-source localization robot mimicking animal behavior, The Inst. of Electrical Engs. of Japan Sens. Syst., CS-98: 35-40 (1998). (English languange abstract).

Ishigure et al., Development of a detection and source localization system for an early stage of fire, Papers of Tech. Meeting on Chem. Sens. Eng., CHS-05: 21-26 (2005). (English language abstract).

Katsumata et al., An insect-sized atmospheric ion source localization robotfor the evaluation of odor source localization algorithms of insects, Journal of the Robotics Soc. of JP, 27: 711-17 (2009). (English language abstract).

Katsumata et al., Atmospheric-ion-cource localization robot mimicking insect odor orientation, Annual Conf. of the Robotics Soc. of Japan Yokoshu, 26: rombunnno.3h1-02 (2008). (English language abstract).

Nakayama et al., Performance of the odor/gas plume tracking robot with transient-response-based algorithm, Natl. Conv. Record I.E.E., 2002: 148 (2002).

Ogami et al., Odor source searching robot, The JP Soc. of Mech. Eng. Robotics Mechatronics, 2003: 1P1.1F.D2(1)-1 P1.1 F.D2(2) (2003).

Ohashi et al., Autonomous wheeled underwater robot mimicking olfactory search behavior of crayfish, The JP Soc. of Mech. Eng., 8:147-48 (2008). (English language abstract).

Sakata et al., Chemical source localization using underwater compass system, Papers of Tech. Meeting on Chem. Sens. Eng. CHS-03: 75-80 (2003). (English language abstract).

The extended European Search Report issued on May 14, 2014, by the European Patent Office in corresponding European Patent Application No. 10838968.5 - 1712. (5 pages).

Ishida et al., "Mobile robot navigation using vision and olfaction to search for a gas/odor source" Autonomous Robots, (Jun. 2006), vol. 20, Issue 3, pp. 231-238.

Office Action with Search Report issued on May 4, 2014, by the Chinese Patent Office in corresponding Chinese Patent Application No. 201080064587.2. (6 pages).

* cited by examiner

ROBOT

TECHNICAL FIELD

The present invention relates to a robot that detects chemical substances.

BACKGROUND ART

WO2006/013396 (Japanese Patent Publication No. 2008-508693) discloses an ion mobility spectrometer with an ion filter in the form of at least one ion channel that includes a plurality of electrodes. WO2005/052546 (Japanese Patent Publication No. 2007-513340) discloses an ion mobility-based system, method, and apparatus for analyzing samples.

DISCLOSURE OF THE INVENTION

The olfactory sense is defined as one of the senses and is realized by receiving molecules of specified chemical substances at receptors. The present invention has an object of providing a robot equipped with an ability that corresponds to the olfactory sense.

One aspect of the present invention is a robot, that is, a programmable mechanical apparatus, including a plurality of sampling points. Such robot includes: at least one detection unit that acquires chemical substance-related information relating to chemical substances included in a fluid at the plurality of sampling points; and an event monitoring unit that determines an occurrence of an event and an occurrence direction of the event relative to the robot on the bases of a change in the chemical substance-related information respectively acquired at the plurality of sampling points. Here, a "change in the chemical substance-related information" includes a change in the chemical substance-related information due to the inclusion of a new chemical substance in the fluid, a change in the chemical substance-related information due to a change in the concentration of chemical substances, and the like. By detecting chemical substances included in a fluid such as air at the plurality of sampling points provided on a single robot, it is possible to infer the direction of a source of the chemical substances. For this reason, it is possible to infer the occurrence direction of the event where the detected chemical substances are present.

The robot should preferably include a moving unit (transportation unit, traveling unit) that moves (transfers, transports) the robot in the occurrence direction of the event. By moving in the event occurrence direction where it was inferred that the event occurred, that is, by turning or transferring, the concentration of the chemical substances that can be detected by the robot will normally increase. Accordingly, it is possible to infer the occurrence direction of an event even more precisely. It is also possible to confirm the source of an event and to track the source of an event.

The robot should preferably further include a cause estimating unit that determines an occurrence cause of the event from the acquired chemical substance-related information (i.e., a change in the chemical substance-related information). By turning in the occurrence direction of an event and/or approaching the source, it is possible to improve the estimation precision of the occurrence cause of the event.

The robot should preferably further include an alarm issuing unit that outputs a warning relating to the occurrence cause of the event as information that can be recognized at least one of visually and audibly. By doing so, it is possible to output a warning when it has been inferred that the event poses some kind of threat.

The robot should preferably also include an information acquiring unit that acquires event appended information including at least one of images and sound in the occurrence direction, a location of the robot, a bearing of the occurrence direction, a movement direction of the fluid, and environment data around the robot. Since it is possible to infer the occurrence direction of the event, it is possible to acquire event appended information including images, sounds, and the like in such direction.

The robot should preferably also include a cause estimating unit that determines the occurrence cause of the event on the bases of the acquired chemical substance-related information and the event appended information. By taking into account the event appended information including images and sound in the event occurrence direction and the like, it is possible to estimate the occurrence direction of the event even more precisely.

The robot should preferably also include a communication unit transferring event information including the occurrence of an event to the outside. The communication unit may be wired or wireless. The communication unit may be a unit capable of accessing an intranet or the Internet.

The robot should preferably also include an alarm issuing unit that acquires the occurrence of the event via the communication unit and outputs a warning relating to the occurrence cause as information that can be recognized at least one of visually and audibly. Since it is possible via the communication unit to use external resources to estimate the occurrence cause, it is possible to improve precision when inferring the occurrence cause.

The robot should preferably also include a moving unit that moves (transfers, travels, transports) the robot in the occurrence direction of the event and a control unit that exchanges information with another robot via the communication unit and controls a moving unit so as to link up with the other robots. By sharing information on the event occurrence direction with a plurality of robots, it is possible to precisely specify the source of the event. Also, if the source of the event moves, it is possible to track such movement and/or surround the source.

The communication unit should preferably include a visible light communication unit. This makes it possible to limit the range of communication, which facilitates improvement in communication precision. It also makes it easier to keep the information being exchanged secret.

The robot should preferably also include a moving unit that moves the robot; and an odor outputting unit that emits chemical substances that form a source of a predetermined odor. By placing an odor, it becomes possible for a robot equipped with the same functions to track this robot.

The at least one detection unit may include a plurality of detection units that respectively correspond to the plurality of sampling points. The at least one detection unit may include a shared detection sensor that is shared between the plurality of sampling points and a supply unit that supplies the fluid from a plurality of sampling points to the shared detection sensor according to time division. A typical detection sensor is an ion mobility sensor (IMS).

Another aspect of the present invention is a method of controlling a robot including determining an occurrence of an event and an occurrence direction of the event relative to the robot on the basis of a change in the chemical substance-related information respectively acquired at the plurality of sampling points.

Yet another aspect of the present invention is a program (or program product) controlling a robot. The robot includes a memory, a CPU, a plurality of sampling points, and a detection unit acquiring chemical substance-related information relating to chemical substances included in a fluid at the plurality of sampling points, and the program includes an instruction that has the robot determine an occurrence of an event and an occurrence direction of the event relative to the robot based on a change in the chemical substance-related information respectively acquired at the plurality of sampling points. The program (or program product) can be provided having been recorded on a recording medium or via a computer network.

DETAIL DESCRIPTION

Figure 1:
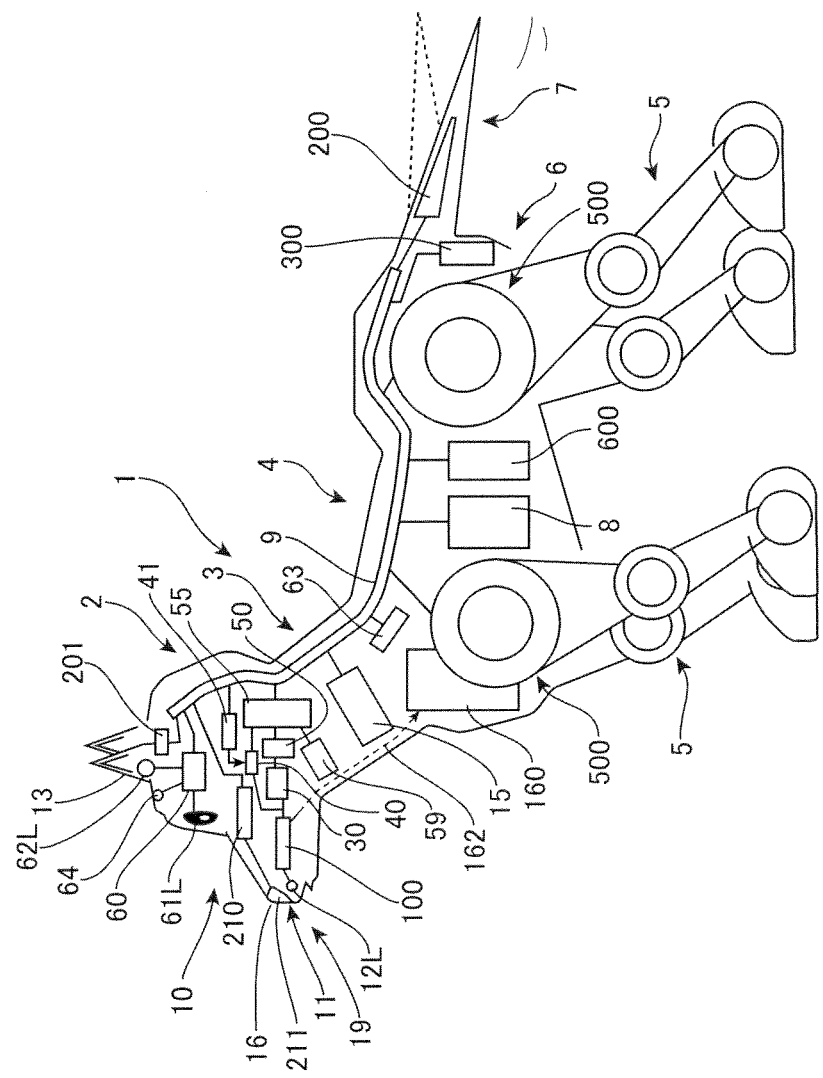
FIG. 1 is a block diagram showing the major elements of a robot dog.
Figure 2:
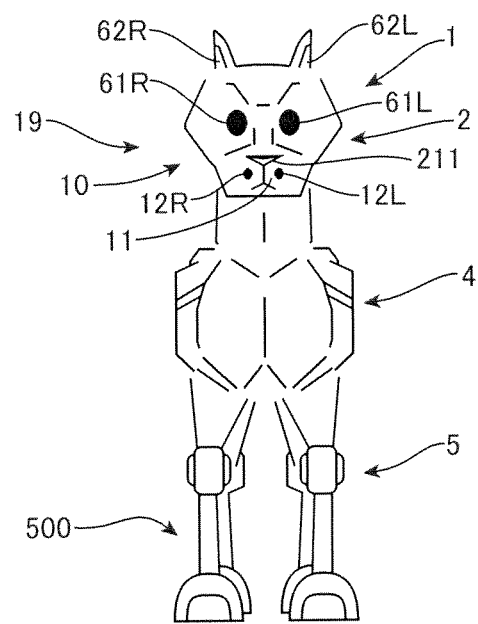
FIG. 2 is a view showing the robot dog from the front.
Figure 3:
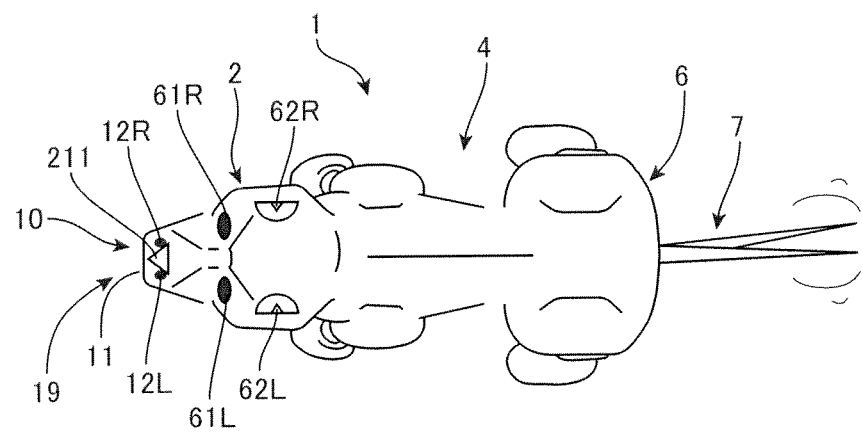
FIG. 3 is a view showing the robot dog from above.

FIG. 1 shows the outlines of a dog-shaped robot (or "robot dog") equipped with an olfactory sense. FIG. 2 shows the appearance of the robot dog when looking from the front. FIG. 3 shows the appearance of the robot dog when looking from above.

The robot dog 1 has an olfactory ability based on an IMS (Ion Mobility Spectrometry)-type sensor (or "detection unit") and, by comparing the output of the sensor with a chemical substance database and also communicating with a plurality of other robot dogs, is capable of specifying and analyzing a target chemical substance and tracking and/or chasing after a moving body (or criminal). Note that the olfactory sense is defined as one of the senses and is realized by receiving molecules of specified chemical substances at receptors. Accordingly, although the detection of chemical substances included in the atmosphere (air) or the like is described below as an "olfactory sense" or "odors/smells", in the system (apparatus or robot) described below, it is also possible to detect chemical substances that cannot be detected by animals as an odor.

Smells and odors are caused by chemical substances such as compounds and gases included in air in the periphery. In the present specification, the expression "chemical substance" includes compounds, molecules, and elements, and includes products without being limited to constituents or compositions. The expression "chemical substances" also includes organic and inorganic substances. It is said that many chemical substances capable of being detected by the olfactory sense include functional groups. One functional group is hydrocarbons, with an example of such being alkanes (chained saturated hydrocarbons). This group includes ethane, methane, propane, butane, and the like as chemical substances. The functional groups are not limited to hydrocarbon groups, and the amino group and the like can be given as an example of a functional group containing nitrogen and the alcohol group and the ketone group can be given as examples of functional groups that contain oxygen. These are mere examples of chemical substances and functional groups. It is believed that the atoms in molecules of a functional group are subject to the same or similar chemical reactions and exhibit a characteristic in having a common odor. Volatile organic materials and organic compounds typically stimulate the olfactory sense as odors. The chemical substances may be gases (i.e., a gas itself) such as carbon monoxide or carbon dioxide. The chemical substances may also be inorganic substances, such as carbon, aluminum, or nitrogen.

One analyzer that is compact, portable, and capable of detecting the cause of an odor is an ion mobility sensor, which has been provided as a chip-type device using MEMS. An ion mobility sensor (or "ion mobility spectrometer") ionizes substances (molecules) present in the air and outputs a spectrum (output pattern or air quality pattern) based on differences in mobility between the ionized molecules, with field asymmetric waveform ion mobility spectrometry (FAIMS) and differential ion mobility spectrometry (DIMS) as known methods.

A spectrometry-type sensor of this type, hereinafter referred to in general as an "IMS sensor", inputs ionized molecular flows into an asymmetric electric field that changes from low voltage to high voltage and outputs the result of filtering such flows based on field mobility of the ions. The "micro DMx" made by SIONEX and the FAIMS device made by OWLSTONE can be given as examples of compact IMS sensors that are commercially available.

In an IMS sensor, as information relating to chemical substances included in a fluid (typically a carrier gas such as air or nitrogen gas), it is possible to detect an ion current that changes in accordance with the two variables of the voltage Vd (dispersion voltage or electric field voltage (Vrf), alternating current) and the voltage Vc (compensation voltage, direct current). Accordingly, three-dimensional data (waveform data, spectra) including such information and two-dimensional spectra where a parameter in one of the three dimensions is fixed are obtained as information relating to chemical substances. It is also possible to acquire a spectral signature (spectral characteristics and features) that shows the elements of a spectrum as information related to chemical substances. As one example, a spectral signature includes a spectral peak amplitude, spectral peak width and spectral peak slope, spectral peak interval, number of spectral peaks, relative positional shift of spectral peaks due to changes in processing conditions, spectral discontinuity points, a Vrf to Vcomp characteristic, and the like.

The detection unit (sensor) that obtains information relating to the chemical substances may be a mass spectrometry-type sensor so that M/Z (mass-to-charge) is obtained as the information related to the chemical substances (chemical substance-related information) included in the fluid.

An analysis-type sensor that uses ion mobility or the like has widespread applicability compared to a sensor that is sensitive to specific constituents (chemical substances) and is capable of detecting the presence and intensity (concentration) of almost all constituents with a similar level of precision in the range where analysis is possible. The information on chemical constituents (chemical substances) detected by the sensor includes intensity variations (which include concentration variations, presence variations, and other changes and variations detected by the sensor) of chemical substances (which includes at least one of compounds, molecules, and elements). As the detection sensor that acquires information related to chemical substances, it is possible to use a wide variety of sensors including a chemical sensor that conforms to IEEE 1451, a liquid crystal sensor (or QCM (Quartz Crystal Microbalance)), an electrochemical sensor, a SAW (Surface Acoustic Wave) device, an optical sensor, gas chromatography, liquid chromatography, and a MOS (Metal Oxide Semiconductor) sensor.

When broadly divided, the robot dog 1 includes, a head portion 2, a neck portion 3, a trunk portion 4, a leg portion 5, a rump portion 6, and a tail portion 7. The robot dog 1 includes an internal bus 9 that passes through the head portion 2, the neck portion 3, the trunk portion 4, and the rump portion 6 to reach the tail portion 7 and distributes data and power, so that the various functions (functional units) incorporated in the robot dog 1 are capable of communicating with one another. A battery 8 is housed in the trunk portion 4 so that the robot dog 1 is capable of moving freely on its own. In addition, the robot dog 1 is equipped with various external communication units so that the robot dog 1 is capable of communicating with other robot dogs, a host apparatus, and with various hardware resources that are capable of being accessed via a computer network.

Note that although the following explanation describes a case where units equipped with various functions are housed in the robot dog 1, the locations at which such units are housed are not limited to the locations in the following explanation. Such functions (functional units) are typically realized by software and programmable hardware resources including one or a plurality of CPUs and memory. Such programmable hardware resources may include a chip such as a dedicated ASIC and may include a chip on which circuits are reconfigurable.

This robot dog 1 includes a detection unit 100 that detects chemical substances included in a fluid at a plurality of sampling points. In the present embodiment, the detection unit 100 includes an IMS sensor and is sometimes referred to hereinafter as the "IMS unit". The robot dog 1 also includes an event monitoring unit 30 that determines an occurrence of an event and the occurrence direction of the event relative to the robot dog 1 based on at least one of changes in the chemical substances detected at the respective sampling points and changes in the concentration of the detected chemical substances. More specifically, the left and right nostrils 12L and 12R of the nose 11 on the front surface 10 of the head portion 2 of the robot dog 1 are sampling holes and the detection unit 100 is housed behind the nose 11. The detection unit 100 may output information on the chemical substances themselves or may output information that changes (varies) according to the presence of chemical substances, that is, "chemical substance-related information".

As the chemical substance-related information, as described earlier, the IMS unit 100 is capable of obtaining a spectrum and/or a spectral signature (hereinafter collectively referred to as "IMS data"). The event monitoring unit 30 determines whether an event has occurred according to changes in the chemical substance-related information.

Figure 4:
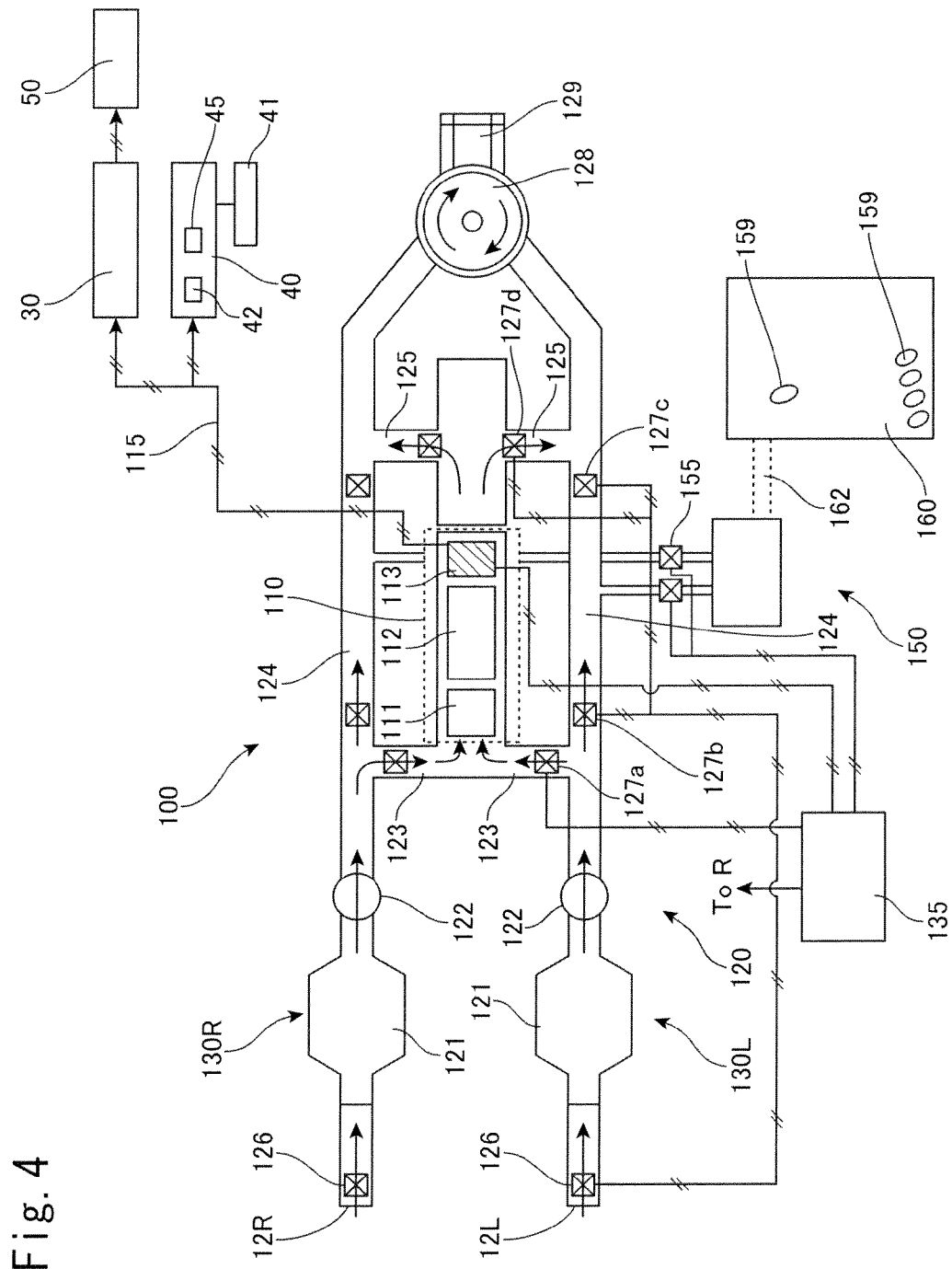
FIG. 4 is a block diagram showing a detection unit.

The IMS unit 100 may include a plurality of IMS sensors attached respectively to the left and right nostrils 12L and 12R that are the sampling points. FIG. 4 shows one example of the detection unit 100 that includes an IMS sensor 110 that is shared between the left and right nostrils 12L and 12R. That is, the detection unit 100 includes the IMS sensor 110 that is shared between the plurality of sampling points 12R and 12L, a supply unit 120 that supplies fluid (in the present embodiment, air (external air) 19 to the IMS sensor 110 according to time division from the plurality of sampling points 12R and 12L), and a sample storage unit 150 that is capable of sealing and storing the external air 19 in sample storage capsules 159.

The IMS sensor 110 includes an ionizing unit 111 that ionizes the chemical substances included in the drawn-in external air 19 using radiation, light, an electric field, or the like, an electric field control filter 112 that controls the movement of the ionized chemical substances, and a unit 113 that outputs IMS data 115 as information relating to the chemical substances included in the external air 19 based on the moved amounts of the ionized chemical substances.

The supply unit 120 includes a suction fan (suction pump) 128 for drawing in the external air 19 from the left and right nostrils 12L and 12R that are the sampling points and discharging the external air 19 from a discharge outlet 129 and ducts 130L and 130R that lead the external air 19 from the left and right nostrils 12L and 12R to the IMS sensor 110 according to time division. The left and right ducts 130L and 130R have the same construction and each include a suction chamber 121, a movable connector 122, a supply tube 123 that supplies the external air 19 to the IMS sensor 110, a bypass tube 124 that bypasses the supply tube 123, and an exhaust tube 125 for exhausting air from the IMS sensor 110. The movable connector 122 is provided to change the orientation of the left and right nostrils 12L and 12R of the nose that are the sampling points by around ±15° (this is not a limitation) in the up, down, left, and right directions. Accordingly, it is possible to change the orientation of the sampling points 12L and 12R without moving the neck portion 3.

A shutoff damper 126 is provided in each of the left and right nostrils 12L and 12R and is capable of shutting off the detection unit 100 from the external air 19. Dampers 127a to 127d are provided on the supply tube 123, the bypass tube 124, and the discharge tube 125 so that such tubes can be separated. The detection unit 100 further includes a control unit 135 that controls such dampers 126 and 127a to 127d and the IMS sensor 110.

For example, when drawing in and analyzing the external air 19 from the left nostril 12L, the dampers 127a to 127d of the right duct 130 are closed and the dampers 127a to 127d of the left duct 130 are opened to purge the lines. Next, the dampers 127a to 127d of the right duct 130R are closed and the chemical substances included in the external air 19 drawn in from the left nostril 12L are detected by the IMS sensor 110. The IMS data 115 is supplied to the event monitoring unit 30 and a search target detection unit 40.

If an event and a search target have not been detected at the event monitoring unit 30 and the search target detection unit 40, air is drawn in and analyzed in the same way as described above from the right nostril 12R.

On the other hand, if an event has been detected by the event monitoring unit 30 but the event cause cannot be inferred at an event cause estimating unit 50, there is the possibility that the chemical substances included in the external air 19 are unconfirmed or are substances that have not been previously analyzed by the IMS sensor 110. Accordingly, before advancing to analysis of the right nostril 12R, the control unit 135 opens the damper 155 that had shut off between the bypass tube 124 and the sample storage unit 150 and has the external air 19 accumulated in the bypass tube 124 sealed by the sample storage unit 150 in a sample storage capsule 159. The capsule 159 is then stored via a capsule discharging route 162 in a stocker 162. By subsequently using an IMS sensor 110 of the same type and a high-precision mass analyzer of a suitable type or the like to analyze the external air 19 sealed in the sample storage capsules 159 stocked in the stocker 160 and adding to a chemical substance database, it is possible to subsequently analyze chemical substances that the IMS sensor 110 provided in the robot was unable to analyze at the time of sampling.

The IMS data 115 for the left and right sampling points 12L and 12R obtained by the substance detection unit 100 is transmitted to the event monitoring unit 30. The event monitoring unit 30 determines whether an event has occurred according to changes in the IMS data 115 of the external air 19 sampled at the respective left and right sampling points 12L and 12R. A change in the IMS data 115 that is the chemical substance-related information implies at least one of a change in the chemical substances and a change in the concentration of the chemical substances included in the external air 19 at the sampling points 12L and 12R. The event monitoring unit 30 compares the IMS data 115 for the previous sampling and the IMS data 115 for the present sampling and determines that an event has occurred when the difference exceeds a threshold set in advance in the event monitoring unit 30.

The "event" in such a case includes various situations such as the releasing of a new chemical substance to the external air 19 and the releasing of a large amount of a chemical substance into the external air 19. Examples of events include the placement of something with an odor, the appearance of something accompanied by an odor, and a happening that is accompanied by an odor. Here, the expression "odor (smell)" is not limited to odors that can be felt by humans and may include chemical substances included in the external air 19 with a concentration that can be detected by the IMS sensor 110. The expression "something accompanied by an odor" includes dangerous substances such as pollutants, explosives, and narcotics, and living creatures such as humans. The expression "happening that is accompanied by an odor" includes a shooting and a fire.

In addition, the event monitoring unit 30 determines the occurrence direction of an event relative to the robot dog 1. The event monitoring unit 30 is capable of determining the occurrence direction of an event by acquiring stereo-type chemical substance detection information. From the time difference and/or concentration difference between the chemical substances detected at the plurality of sampling points 12L and 12R and the three-dimensional positional relationship between the plurality of sampling points 12L and 12R, it is possible to determine (estimate) the occurrence direction of the event. With the robot dog 1, although the left and right nostrils 12L and 12R of the nose 11 are used as the sampling points, it is also possible to provide sampling points at more distant positions. For example, by setting the holes of the ears 13 as sampling points or adding the holes of the ears 13 to the nose 11 as sampling points, it is possible to improve the determination precision for an event in the up-down direction.

The positions where sampling points are provided to detect chemical substances are not limited to the head portion 2 and may be provided at other locations, such as by being provided on the trunk portion 4 or being provided on the rump portion 6, for example. Also, the detection unit 100 provided on the robot dog 1 is not limited to a single unit and units may be separately provided in the head portion 2, the trunk portion 4, and the rump portion 6.

The robot dog 1 further includes a moving unit (transporting unit, traveling unit, transferring unit) 500 capable of moving or transporting the robot dog 1 in a freely chosen direction by moving the leg portion 5. By using the moving unit 500, the robot dog 1 is capable of turning in the occurrence direction of an event, moving closer or further away in the occurrence direction of the event, and moving so as to maintain the same distance from an event occurrence point. The robot dog 1 includes a central control unit 55 including hardware resources such as a CPU and a memory and moves the robot dog 1 toward the event occurrence direction obtained from the event monitoring unit 30. If the robot dog 1 moves in the inferred event occurrence direction when an event has occurred, the concentration of the chemical substances included in the external air 19 will normally rise. Also, if the movement or traveling direction is incorrect, the concentration of the chemical substances will normally fall, which makes it possible to determine that the inferred event occurrence direction is erroneous. Accordingly, the occurrence direction of an event can be inferred even more precisely. Also, by moving closer to the source of an event, it is possible to acquire an image of the source of the event using an image acquisition unit 61, described later, and to track the source of the event.

The robot dog 1 further includes the cause estimating unit 50 that determines or estimates the occurrence cause of an event from the IMS data 115 obtained by the chemical substance detection unit 100. The cause estimating unit 50 includes a database storing a variety of patterns corresponding to the IMS data 115 and is capable of analyzing the IMS data 115 using an analysis technique such as pattern matching and of estimating the cause of the IMS data 115 or of changes thereto. The cause estimating unit 50 may also obtain the occurrence cause of an event by sending the IMS data 115 via various types communication units, described later, to external hardware resources, for example, an analysis server. The robot dog 1 is capable of approaching the source of an event and of acquiring IMS data 115 corresponding to chemical substances of a higher concentration. Accordingly, it is possible to improve the estimation precision of the occurrence cause of an event.

The cause estimating unit 50 is also capable of dynamically changing a priority order table and rules included in the cause database via the communication units and the network. As one example, if the event that has been detected by the event monitoring unit 30 is related to one particular chemical substance, it is preferable to dynamically change the database so as to become sensitive to elements relating to the chemical reactions that may happen accompanying the detected chemical substance and are subject to dangerous chemical reactions that produce an extremely large amount of reactive energy or heat. It is also desirable for spatial data on the region or factory ("monitored region") monitored by the robot dog 1 to be inputted in advance into the database to make it possible to predict damage that will occur to the monitor region if the event detected by the event monitoring unit 30 gradually develops and to give a warning or notification.

The priority order in the cause database of the oxygen concentration or CO concentration or of chemical substances that are poisonous or harmful to humans may be changed from the outside via a communication unit. For an unmanned factory for example, there is the fundamental case of explosive substances and other problematic substances that can cause extensive damage to structures. For a situation where a specified chemical substance is being produced or handled, there is also the case where a problematic chemical substance can be produced by a chemical reaction that occurs when the presence of a certain chemical substance becomes too great. In such situations or conditions, the operation of the robot dog 1 can be dynamically controlled.

In addition, the robot dog 1 includes the search target detection unit 40 that operates in parallel with the cause estimating unit 50. The search target detection unit 40 includes a local memory 41 that stores a library including specified patterns produced by converting (reverse converting) causes including chemical substances to be searched for to IMS data 115, a matching unit 42 that routinely or steadily matches the specified patterns against the IMS data 115 according to an analysis technique such as pattern matching, and an alarm unit 45 that outputs an alarm when a specified pattern and the IMS data 115 match or a specified pattern is included in the IMS data 115.

Representative examples of search targets include toxic substances that pose a threat to humans, explosives, weapons, drugs such as illegal narcotics, criminals who are being tracked, and missing persons. By storing the IMS data 115 outputted when the IMS sensor 110 has detected the unique odors of such search targets in advance in the local memory 41, it is possible for the robot dog 1 to find such search targets more effectively.

The robot dog 1 further includes an alarm issuing unit 59 that outputs a warning relating to the occurrence cause of an event as information (alarm information) that can be recognized at least one of visually and audibly. If an event detected by the event cause estimating unit 50 or the search target detection unit 40 is inferred to be an event that carries some kind of threat, the alarm issuing unit 59 is capable of outputting a warning by way of sound, light, or the like.

The robot dog 1 further includes the information acquisition unit 60 that detects event appended information including at least one of kinds of information such as images and sound in the occurrence direction, the location of this robot, the bearing of the occurrence direction, the moving direction of the fluid, and environmental data for the periphery of this robot. Since the robot is capable of inferring the occurrence direction of an event, it is possible to acquire event appended information including images and sound for such direction.

The robot dog 1 includes image acquisition units 61L and 61R that acquire left and right images at the positions of the left and right eyes on the head portion 2. The image acquisition units 61L and 61R are capable of obtaining not only three-dimensional images in the range of visible light but are also capable of obtaining three-dimensional images in the range of infrared light and are therefore able to see in the dark. The image acquisition units 61L and 61R may also be provided with other abilities including the ability to measure distance. The robot dog 1 also includes microphones 62L and 62R that acquire left and right sound (i.e., stereo sound) at the positions of the left and right ears 13 on the head portion 2. The robot dog 1 is capable of moving the head portion 2 up, down, to the left, and to the right relative to the trunk portion 4 by way of an actuator 15 provided in the neck portion 3. Accordingly, by orienting the head portion 2 in the event occurrence direction, it is possible to obtain images and sound in the event occurrence direction.

In addition, the robot dog 1 includes a GPS unit 63 and is capable of including a global position of the robot dog 1 in the event appended information. The robot dog 1 includes an environment measuring unit 64 that includes wind direction, temperature, and humidity, and is capable of including such information in the event appended information.

The event appended information is supplied to the cause estimating unit 50. The cause estimating unit 50 is capable of estimating the occurrence cause of the event more precisely by taking into account the event appended information that includes images and sound in the event occurrence direction and the like.

The robot dog 1 further includes various types of communication unit 200, 201, and 210 that transfer event information including the occurrence of an event to the outside. First, the tail portion 7 of the robot dog 1 forms the RF communication unit 200 that uses the FM and AM frequency bands. The left and right ears 13 form a MIMO-type communication unit 201 for transmitting and receiving large amounts of information. In addition, the nose 11 forms a directional communication interface 211, with a directional communication unit 210 being housed behind the nose 11. The directional communication interface 211 includes a laser communication-type semiconductor laser, a visible light communication LED, a light-receiving unit, an ultrasound emitting apparatus for ultrasonic communication, and a microphone. By moving the actuator 15 of the neck portion 3, it is possible to point the directional communication interface 211 in a desired direction and limit the range of communication, which facilitates improvement in communication precision. It also makes it easier to keep the information being exchanged secret.

Via such communication units 200, 201, and 210, it is possible to access a computer network such as an intranet or the Internet. Accordingly, the robot dog 1 is capable of using a variety of resources that are available on a computer network. As one example, it is possible to send the IMS data 115 via a computer network to a cause determining server and to obtain the occurrence cause of the event using external resources. Since it is possible via the communication units 200, 201, and 210 to use external resources to estimate the occurrence cause, it is possible to improve the estimation precision for the occurrence cause.

Also, by using the communication units 200, 201, and 210, the robot dog 1 exchanges information with other robot dogs to specify the source of an event through cooperative (linked) operation and when the source of an event poses a threat, it is possible to confront such threat. That is, the central control unit 55 controls the moving unit 500 so as to make movements that are coordinated with other robot dogs 1. By sharing information on the event occurrence direction with a plurality of robot dogs 1, it is possible to precisely specify the source of the event. Also, if the source of an event moves, it is possible to track such movement or to surround the source.

The robot dog 1 further includes an odor output unit 300 that releases chemical substances which are a source of a specified odor. By placing an odor that can identify the robot dog 1 at a specified target location during movement, it becomes possible to cause a robot dog 1 equipped with the same functions to track the present robot dog 1. By using an unnoticeable odor that humans are incapable of recognizing or an odor that is not distinctive enough to be distinguished from the background odor, it is possible to indirectly inform other robot dogs 1 of the movement path or the like of the robot dog 1.

In addition, the robot dog 1 includes a countermeasure unit 600 that eliminates threats when the cause specified by the event cause estimating unit 50 is a threat that can be handled by the robot dog 1. One example of the countermeasure unit 600 is a fire extinguisher. If the cause of the event is a fire that can be extinguished at an initial stage, such event can be solved by the robot dog 1. Another example of the countermeasure unit 600 is a unit capable, when the cause of an event is a dangerous chemical reaction, of spraying a derivative capable of inducing a different chemical reaction that cancels out the dangerous chemical reaction. The countermeasure unit 600 may also be a unit that reduces the concentration of a dangerous chemical substance using nitrogen gas or an inert gas, or that reduces the concentration of oxygen. The countermeasure unit 600 may be a lifesaving emergency unit, which includes an oxygen tank, pharmaceuticals, food, and the like.

Figure 5:
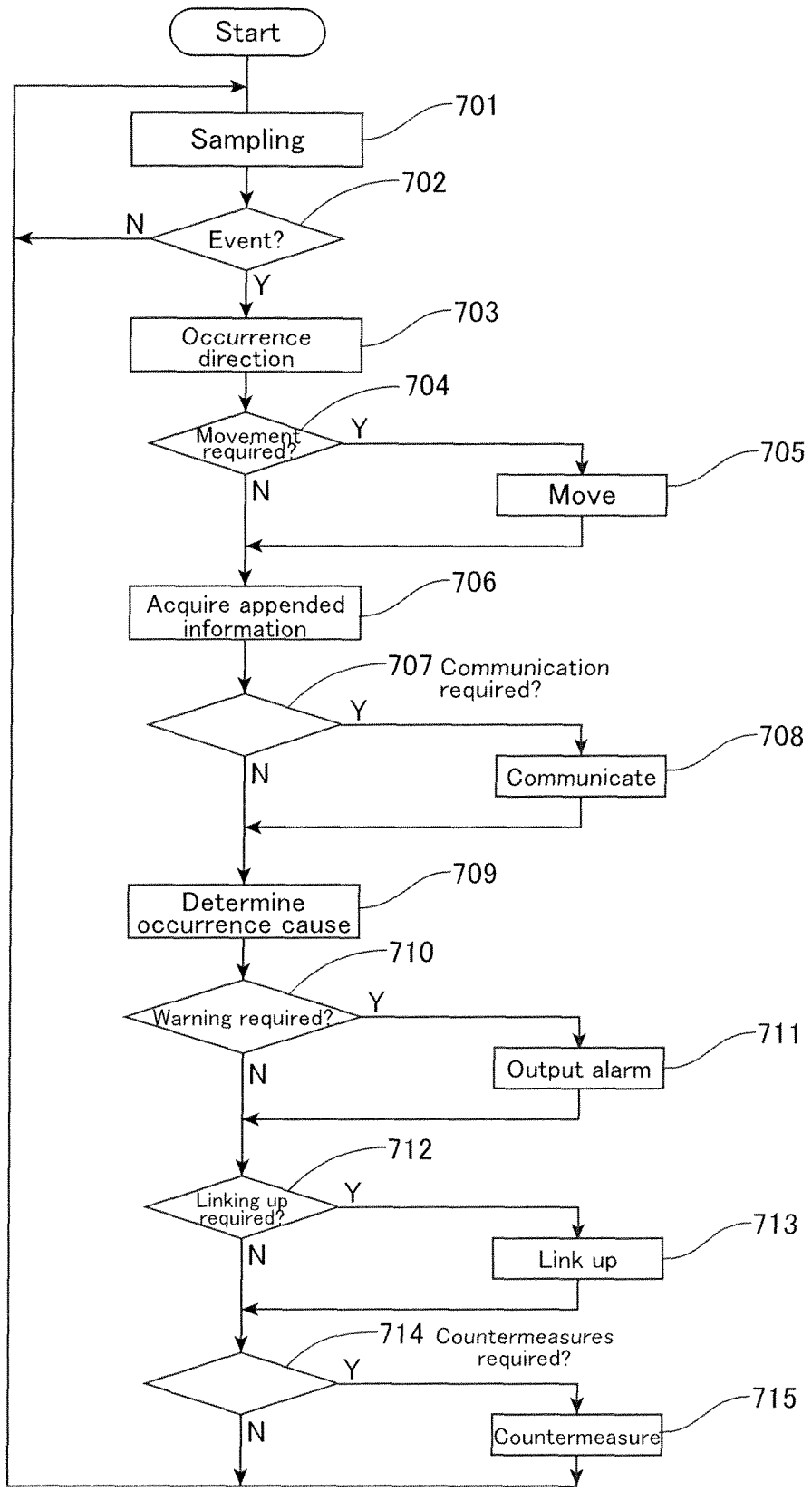
FIG. 5 is a flowchart showing an overview of control of the robot dog.

FIG. 5 shows typical control of the robot dog 1 by way of a flowchart. Such control can be provided via a computer network or be recorded on a recording medium as a program (program product).

In step 701, sampling is carried out by the detection unit 100 at a plurality of sampling points. In step 702, the event monitoring unit 30 determines that an event has occurred from at least one of a change in the chemical substances or a change in concentration of a chemical substance in the fluid (air) that are shown or included in the IMS data 115. In addition, if the occurrence of an event has been recognized, in step 703 the event monitoring unit 30 determines the occurrence direction of the event relative to this robot dog 1.

If the central control unit 55 determines in step 704 that it is necessary to move or transport the robot dog 1 in response to the event, in step 705 the robot dog 1 moves or travels in the event occurrence direction using the moving unit 500.

Before and after such processing, or in parallel with such processing, in step 706 the information acquisition unit 60 acquires event appended information including at least one of kinds of information relating to images and sound in the occurrence direction, the location of the robot, the bearing of the occurrence direction, the movement direction of the fluid, and environment data for the periphery of or around the robot dog 1.

In addition, if the central control unit 55 determines in step 707 that support is required from resources such as an external server, in step 708 the event information is transferred together with the event appended information to the outside via the communication unit 200 and the like.

In step 709, the cause estimating unit 50 determines the occurrence cause of the event based on at least one of a change in the chemical substances and a change in the concentration of a chemical substance included in the IMS data 115. The cause estimating unit 50 may acquire the event occurrence cause from an external server or the like.

If, in step 710, the occurrence cause that has been determined or estimated requires a warning, in step S711 the central control unit 55 outputs a warning using the alarm issuing unit 59. By doing so, the presence of a threat in the periphery of the robot dog 1 is indicated. By using the communication unit 200 or the like, it is also possible to inform the outside of the presence of the threat.

If the central control unit 55 determines in step 712 that it is necessary to link up with other robot dogs, in step 713 a coordinated operation with other robot dogs is carried out via the communication unit 200 or the like. The central control unit 55 controls the moving unit 500 so as to link up with other robot dogs 1 or the like. Chemical substances that are the source of a predetermined odor may be emitted from the odor output unit 300 to indirectly transmit information to other robot dogs 1.

In addition, if the central control unit 55 determines in step 714 that the robot dog 1 is capable of handling (carrying out initial response) to the occurrence cause that has been determined or estimated, the countermeasure unit 600 is used to take suitable countermeasures to the occurrence cause. In step 715, the central control unit 55 controls the moving unit 500 to move the robot dog 1 to a suitable position for the countermeasures.

This type of olfactory robot dog 1 has independent left and right nasal cavities and is capable of drawing in and analyzing air by carrying out independent speed control over the air in the olfactory spaces. Normally a minimum of one IMS (sensor) is installed, but two independent sensors may be provided. If one sensor is installed, analysis is carried out according to time division. The olfactory robot dog is provided with a self-storage search mode where the robot dog first searches for chemical substances that are present in its own storage (data), a group-storage search mode where the robot dog communicates with other olfactory robot dogs present in the vicinity and links up to conduct a search, a global search mode where the robot dog carries out a search by remotely accessing chemical substances, an estimation mode where the robot dog analogizes chemical substance information that is not present in storage, a learning mode where the robot dog stores and accumulates new chemical substance information not present in an estimated range, a parallel search mode carried out by a plurality of olfactory robot dogs, and a trace search mode where a moving target is tracked and/or the position of such target is specified.

Since the olfactory robot dog 1 is also capable of transmitting individually the information stored by itself to another olfactory robot dog that requires such information, it is possible to reduce the network overheads and carry out a search in parallel. Since it is also possible to synthesize tiny amounts of chemical substances to create a mock odor based on transmitted odor/fragrance streaming information, it is possible to share the target presently being searched for with humans.

Since the olfactory robot dog 1 will have no fear or emotional reaction to danger at a fire scene or other location that is dangerous due to radiation or explosives, such emotions will not hinder the achievement of objectives. Since the olfactory robot dog is equipped with a visible light communication function in addition to wireless communication, there is almost no leaking of communicated information to superfluous parties and it is possible to communicate at high speed with only other parties in visible range. At a controller that controls an entire group of olfactory robots, it is possible to group together and/or split the olfactory robots as necessary and, by controlling the wavelength of visible light, to dynamically configure teams that are unlikely to intercept each others' information. In particular, by using visible light communication, it is possible to measure position extremely precisely to an accuracy of several tens of millimeters, even in locations where the olfactory robots are incapable of receiving GPS signals.

Conventionally, real dogs have often been used to sniff out and recognize narcotics, explosives and personal articles of criminals, but when a dog is exposed to the same strong odor many times, this results in a drop in the olfactory function of the dog. With metal oxide film-type sensors, such sensors react to only specified chemical substances and there are cost and physical issues when realizing a wide search space. Although a sensor network may function as in the chemical substance specifying process of the robot dog 1 within a given range, such network is not equipped with objective-based modes. There is also the problem that although the olfactory robot dog 1 having mobility and being capable of moving is realized, unless the sensor network is appropriately set up in advance, the efficiency of robot is not so large. In particular, if such networks are not applied, the robots have not had functions for adding, analogizing, and learning new chemical substances, of which an unknown number exist.

The robot dog 1 includes the detection unit 100 that carries out olfactory processing and the control unit 55 that controls such unit and is also capable of being equipped with a reflex response unit that immediately responds to a variety of external stimuli and an intelligence function that carries out estimation, inference, and learning.

The specifying of chemical substances is realized by the function for adjusting the angles of the two independent nasal cavities 12R and 12L, the function for adjusting the suction speed, the internally provided detection unit 100 with humidity controller, and the data processing unit 55, and the like. One characteristic of the olfactory robot dog 1 is that the dog is configured to give priority to process relating to explosive substances that are extremely dangerous and/or poisons, poisonous gas, and harmful substances, so that it is possible, if necessary, to react to an emergency by stopping all analysis and carrying out the prioritized processing.

In addition, the robot dog 1 is equipped with the cause estimating unit 50 that acts as a dedicated danger predicting unit and also the search target detection unit 40 that functions independently, and therefore has a function for continuously monitoring conditions that can pose a threat. When a chemical substance database for search targets of the present robot dog 1 has been loaded into the local memory 41 of the search target detection unit 40 but an unregistered chemical substance has been encountered, it is possible to refer to remotely-located global data either independently or via the event cause estimating unit 50.

In addition, if there is no registration in the global data, the robot dog 1 is capable via the sample storage unit 150 of registering a substance as a new chemical substance. That is, if a cause cannot be determined, instead of having the external air 19 simply discharged from the substance detection unit 100, the external air is switched to the sample storage unit 150 and is stored in a capsule. This is carried out to enable matching against the analysis results of an existing analyzing apparatus at a later time and subsequent registration, which improves the quality of the database. To construct a vast database with appropriate quality, such an automated system is extremely important. To efficiently enhance an IMS-type database, it is possible to build rules for matching the difference information produced when analysis results of existing mass spectrometry apparatuses and the like are compared with analysis results using IMS or for absorbing and compensating for such differences. Since statistical data is accumulated in this way, the building of an IMS database can be automated.

The olfactory robot dog 1 is capable of switching between a plurality of modes according to instructions from an external controller received via the communication unit 200 or the like. The cause estimating unit 50 is capable of storing information on chemical substances that are search targets (analysis targets) and substances of the same system in the search database in the local memory. Accordingly, it is possible to search for the occurrence cause of an event in a short time (self-storage search mode). One example of a search database uses an RD (Relational Database) structure where it is possible to search using a plurality of keys, and it is desirable to use a construction where similar chemical substances, intermediate reactants that are susceptible to chemical changes, and byproducts or the like are disposed short distances apart in the search space.

It is also possible to easily add new and yet to be registered chemical substances to the database by changing the search keys. The olfactory robot dog 1 is also equipped with a mode which is capable, when the robot dog 1 has been externally requested to cooperate in a search which is separate to the self-storage search mode, cooperates with the external search independently of and without interrupting a self-storage search process. This means that the robot dog 1 has a dual-system structure so as to be capable of executing completely independent searches. By doing so, searches are realized through parallel processing where olfactory robot dogs cooperate with one another. Although a common search algorithm is used in a fundamental case, to reduce the search time, it is also possible to provide a mode that accesses the RD structure of a search database while changing the search keys to enable a plurality of olfactory robot dogs to perform a search using different estimates for a single target. If, by doing so, a hit is achieved sooner, it is possible to cancel the other search and start a new search. This means that it is possible to further speed up a parallel search that uses a plurality of robot dogs 1. It is also possible to reduce the search time by logically dividing a search space and applying the divided search spaces to a plurality of olfactory robot dogs 1 respectively for the search.

If a new chemical substance has been detected, the olfactory robot dog 1 provisionally registers the substance via a network in a global memory. With this method, if the substance is later specified by carrying out component analysis, proper registration is carried out. A signature of the chemical substance is registered and substances are estimated using a given estimation algorithm. Such estimation uses an arrangement where the algorithm and estimation reasoning (rules) are modified to improve the accuracy using statistical processing and the results of specifying the actual substances. This is referred to as the estimation and learning of chemical substances and contributes to reducing the time required for humans to specify chemical substances. In other words, this contributes to advancing from a semi-automated algorithm to a fully automated algorithm. To increase the estimation accuracy and learning efficiency, it is extremely important to discover not only the signature information of the search target but also other information at such location, such as humidity and temperature and factors that fall into the gap between actual analysis results and analogizing including correlation with other signatures present at such location.

Note that a robot dog has been described above as an example of a robot that is capable of moving independently, that is, a programmable mechanical apparatus. Such robot may be capable of freely moving by itself like an animal or may be a robot that has a premise of being connected to a network and does not transfer to cover any distance, for example, by only revolving or moving up and down. By estimating the occurrence direction of the event and taking action such as changing the orientation, it is possible to acquire images and sound for the occurrence direction of the event. Accordingly, by using a robot, it is possible to determine the cause of an event with overall consideration not just to information on chemical substances but also other information such as images and sound.

Also, although the robot dog is one example of a robot capable of moving on the ground, the robot may be a robot bird or a robot that is capable of floating or flying in the air. In addition, the robot may be a robot that moves over or under the sea. Also, although a robot including a function that detects chemical substances present in a gas has been described above as an example, the robot may include a function that detects chemical substances included in water or in the sea.

The invention claimed is:

1. A robot including a plurality of sampling points, comprising:
    a detection unit that acquires chemical substance-related information relating to chemical substances included in a fluid at the plurality of sampling points, the detection unit including a sensor outputting spectral data including changes in concentration of an unspecified number of chemical substances;
    a communication unit that enables communication with another robot;
    a memory that enables storing target chemical data for a search;
    an event monitoring unit that determines an occurrence of an event and an occurrence direction of the event relative to the robot based on a temporal change in a chemical constituent and a temporal change in concentration of each detected chemical substance included in the spectral data of each sampling point,
    means for self-searching for a chemical using the target chemical data in the memory and the spectral data output by the sensor, and
    means for group-searching for a chemical using information transmitted via the communication unit from another robot and the spectral data output by the sensor without interrupting a process of the self-searching means.

2. The robot according to claim 1,
further comprising a moving unit that moves the robot in the occurrence direction of the event.

3. The robot according to claim 1,
further comprising a cause estimating unit that determines an occurrence cause of the event including a type of chemical substance or a type of the event estimated based on the chemical substance-related information of each sampling point.

4. The robot according to claim 3,
further comprising an information acquiring unit that acquires event appended information including at least one of images and sound in the occurrence direction of the event, a location of the robot, a bearing of the occurrence direction of the event, a movement direction of the fluid, and environment data around the robot, and
the cause estimating unit determines the occurrence cause of the event based on the chemical substance-related information of each sampling point and the event appended information.

5. The robot according to claim 3,
further comprising an alarm issuing unit that outputs a warning relating to the occurrence cause of the event and search results of the detection unit as information that can be recognized at least one of visually and audibly.

6. The robot according to claim 1,
wherein the communication unit transfers event information including the occurrence of the event to an outside.

7. The robot according to claim 6,
wherein the event information includes chemical substance-related information, and the robot further comprises an alarm issuing unit that acquires, via the communication unit, an occurrence cause of the event which includes a type of chemical substance or a type of the event estimated based on the chemical substance-related information of each sampling point and outputs a warning relating to the occurrence cause of the event as information that can be recognized at least one of visually and audibly.

8. A robot including a plurality of sampling points, comprising:
a detection unit that acquires chemical substance-related information relating to chemical substances included in a fluid at the plurality of sampling points, the detection unit including a sensor outputting spectral data including changes in concentration of an unspecified numbers of chemical substances;
a memory that enables storing target chemical data for a search;
an event monitoring unit that determines an occurrence of an event and an occurrence direction of the event relative to the robot based on a temporal change in a chemical constituent and a temporal change in concentration of each detected chemical substance included in the spectral data of each sampling point,
wherein the communication unit transfers event information including the occurrence of the event to an outside, the robot further comprising:
a moving unit that causes the robot to move in the occurrence direction of the event; and
a control unit that exchanges information including the occurrence direction of the event with another robot via the communication unit and controls the moving unit so as to link up with the other robot and track movement of a source of the event or surround the source.

9. The robot according to claim 6,
wherein the communication unit includes a visible light communication unit.

10. The robot according to claim 1, further comprising:
a moving unit that moves the robot; and
an odor outputting unit that emits chemical substances that form a source of a predetermined odor.

11. The robot according to claim 1,
wherein the detection unit includes a plurality of detection sensors respectively corresponding to the plurality of sampling points.

12. The robot according to claim 1,
wherein the detection unit includes a shared detection sensor and a supply unit that supplies the fluids from the plurality of sampling points to the shared detection sensor according to time division.

13. The robot according to claim 1,
wherein the plurality of sampling points include at least three sampling points disposed at different positions in three dimensions.

14. A method for controlling a robot,
wherein the robot includes a memory that enables storing target chemical data, a CPU, a plurality of sampling points, and a detection unit acquiring chemical substance-related information relating to chemical substances included in a fluid at the plurality of sampling points, the detection unit including a sensor outputting spectral data including changes in concentration of an unspecified number of chemical substances, and
the method comprises determining an occurrence of an event and an occurrence direction of the event relative to the robot based on a temporal change in a chemical constituent and a temporal change in concentration of each detected chemical substance included in the spectral data of each sampling point,
self-searching for a chemical using the target chemical data in the memory and the spectral data output by the sensor, and
group-searching for a chemical using information transmitted via the communication unit from another robot and the spectral data output by the sensor without interrupting a process of the self-searching means.

15. The method according to claim 14,
further comprising determining an occurrence cause of the event including a type of chemical substance or a type of event estimated based on the chemical substance-related information of each sampling point.

16. The method according to claim 15,
wherein the robot further includes an information acquiring unit that acquires event appended information including at least one of images and sound in the occurrence direction of the event, a location of the robot, a bearing of the occurrence direction of the event, a movement direction of the fluid, and environment data around the robot, and
the determining occurrence cause of the event includes determining the occurrence cause of the event from the acquired chemical substance-related information of each sampling point and the event appended information.

17. The method according to claim 15,
wherein the communication unit transfers event information including the occurrence of an event and chemical substance-related information of each sampling point to an outside, and the determining occurrence cause of the event includes acquiring the occurrence cause of the event via the communication unit.

18. The method according to claim 15, wherein the robot further includes an alarm issuing unit that outputs a warning as information that can be recognized at least one of visually and audibly, and the method further comprises outputting a warning relating to the occurrence cause of the event and a search result of the self-searching and the group searching from the alarm issuing unit.

19. The method according to claim 14, wherein the robot includes a moving unit, and the method further comprises moving in the event occurrence direction using the moving unit.

* * * * *